(12) United States Patent  (10) Patent No.: US 6,692,467 B2
McFarlane  (45) Date of Patent: Feb. 17, 2004

(54) TROCAR ASSEMBLY

(75) Inventor: Richard H. McFarlane, Riviera Beach, FL (US)

(73) Assignee: Taut, Inc., Geneva, IL (US)

( * ) Notice: Subject to any disclaimer, the term of this patent is extended or adjusted under 35 U.S.C. 154(b) by 131 days.

(21) Appl. No.: 09/870,112

(22) Filed: May 30, 2001

(65) Prior Publication Data

US 2002/0019609 A1 Feb. 14, 2002

Related U.S. Application Data

(60) Provisional application No. 60/208,351, filed on May 31, 2000.

(51) Int. Cl.$^7$ ............................................... A61M 5/178
(52) U.S. Cl. ............................ 604/167.03; 604/167.05; 604/264
(58) Field of Search ................................ 604/158, 264, 604/167.01, 167.03, 167.05

(56) References Cited

U.S. PATENT DOCUMENTS

| 4,931,042 A | 6/1990 | Holmes et al. |
| 5,114,407 A | 5/1992 | Burbank |
| 5,224,952 A | 7/1993 | Deniega et al. |
| 5,320,608 A | 6/1994 | Gerrone |
| 5,690,663 A | 11/1997 | Stephens |
| 5,906,595 A | 5/1999 | Powell et al. |
| 6,077,249 A | 6/2000 | Dittrich et al. |

Primary Examiner—Brian L. Casler
Assistant Examiner—Jeremy Thissell
(74) Attorney, Agent, or Firm—Malloy & Malloy, P.A.

(57) ABSTRACT

A trocar assembly structured to regulate fluid flow as well as the introduction of predetermined medical instrumentation into and out of a body cavity of a patient during a surgical procedure such as, but not limited to laparoscopy, endoscopy, etc. The trocar assembly includes a housing having a hollow interior secured at one end to an elongated open ended sleeve through which fluid flow and medical instrumentation passes. A valve assembly includes a valve member disposed within the hollow interior and a valve structure including a valve seat rotatably connected to the housing such that the valve seat is selectively rotatable relative to the valve member and into and out of fluid sealing engagement therewith so as to respectively define a valve-closed position and a valve-open position. The valve assembly may be rotated between the aforementioned open and closed positions utilizing one hand of the person operating the trocar assembly, wherein the valve assembly will automatically remain either in an open or closed position, without continuous pressure being exerted thereon by the personnel operating the trocar assembly.

35 Claims, 5 Drawing Sheets

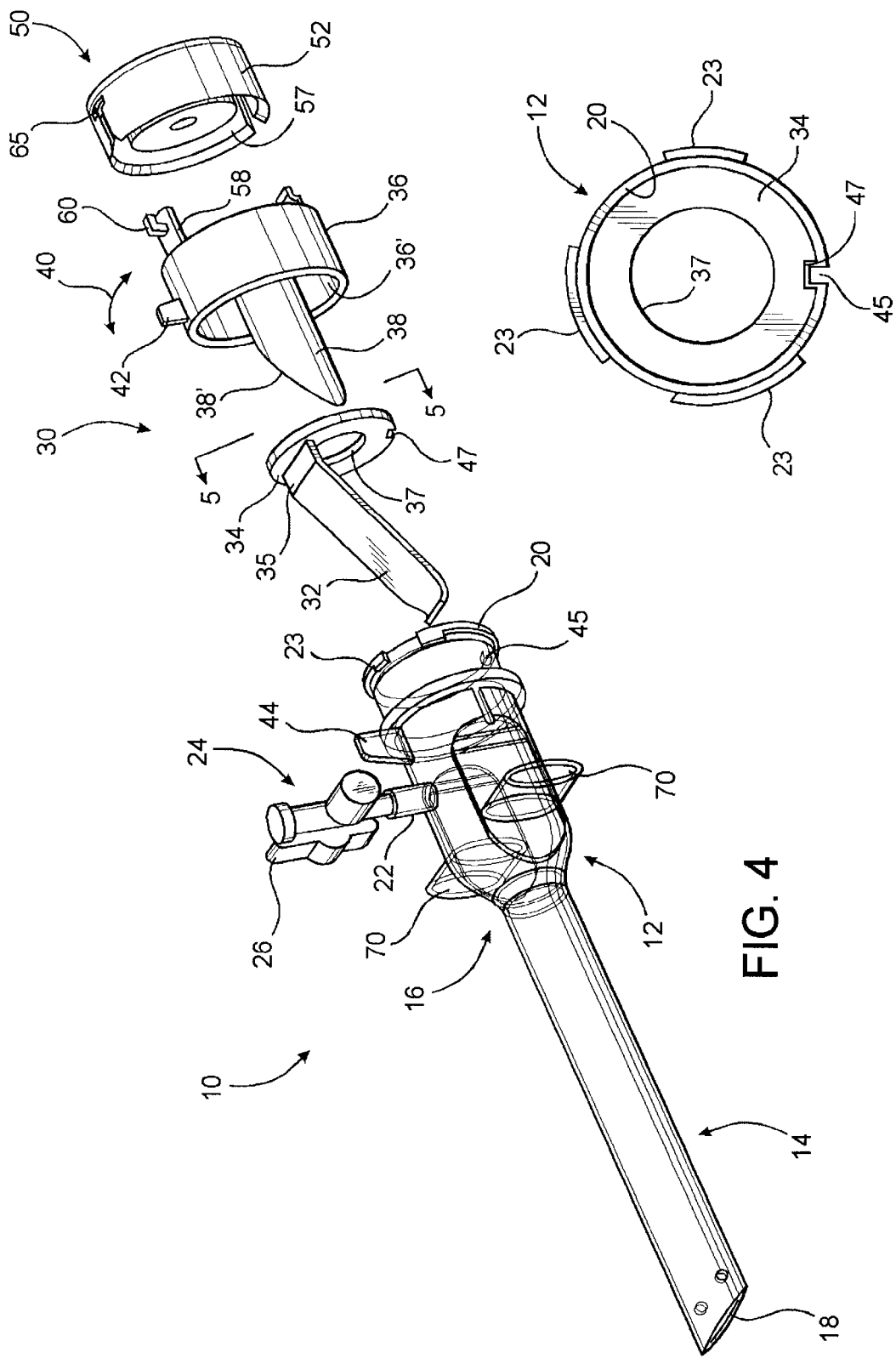

TROCAR ASSEMBLY

CLAIM OF PRIORITY

The present application is based on and a claim to priority is made under 35 U.S.C. Section 119(e) to provisional patent application currently pending in the U.S. Patent and Trademark Office having Serial No. 60/208,351 and a filing date of May 31, 2000.

BACKGROUND OF THE INVENTION

1. Field of the Invention

This invention relates to a trocar assembly structured to facilitate access to internal body cavities of a patient for purposes of performing laparoscopic, arthroscopic, endoscopic or other surgical procedures, wherein inflation and deflation of the body cavity is facilitated by a valve assembly incorporated in the trocar assembly. The valve assembly is selectively positionable between a valve-open and a valve-closed position utilizing a single hand of the operator of the trocar assembly by rotating an externally accessible portion of the valve assembly, wherein the valve assembly is maintained in the preferred open or closed position without external pressure being maintained thereon.

2. Description of the Related Art

In the medical field, the trocar assembly is recognized as an instrument of primary importance when an intended surgical procedure only requires the formation of a small incision to provide access to an internal body cavity or one or more organs located therein. The popularity of modern day trocar assemblies is based in part on technical advances in the medical profession which have reduced the need of surgical procedures involving the forming of substantially large incisions through the body wall or outer bodily tissue, in order to provide access to internal body cavities. It is well recognized, that the forming of large incisions utilized in open surgical procedures are traumatic in nature and significantly increase the time required of a patient to completely recover from a surgical procedure, as well as add to the pain and discomfort during such recuperative period. As a result, laparoscopic, arthroscopic, endoscopic and other surgical procedures involve the formation of one or more small openings in the outer body wall utilizing an appropriate penetrating instrument or obturator, in combination with a trocar assembly.

Another common feature of conventional trocar assemblies is the attachment of a source of pressurized fluid which is forced through the trocar assembly, along an access cannula associated therewith, and eventually into the accessed internal body cavity. Inflation of the body cavity causes its expansion and provides needed space for the physician or other personnel to perform the intended surgical procedure. However, one problem associated with known or conventional trocar assemblies relates to the valve or like fluid flow regulating structure usually connected to the trocar housing and disposed and structured to regulate the flow of fluid both into and out of the accessed body cavity. More specifically, once the body cavity is inflated, for the reasons set forth above, it is important that the fluid pressure within the body cavity be maintained in order to provide the needed access to the internal organs as well as provide adequate room for visual observation, such as during an endoscopic procedure. Therefore, the escape of the pressurized fluid from within the body cavity, back through the access cannula and housing of the trocar assembly, must be prevented by efficient operation of the valve or flow regulating structure associated therewith. Also, once the surgical procedure has been completed it may be advantageous to deflate the body cavity in an effective and efficient manner through manipulation of the valve or flow regulating structure, associated with the trocar.

Naturally, proper positioning and operation of the trocar assembly must be accomplished with great precision and the physician or other medical personnel responsible for its operation should be able to manipulate the valve assembly preferably using only one hand to both hold the trocar assembly and operate the valve structure associated therewith. Also, a problem commonly existing with known trocar assemblies and their associated valve structures is the inability to easily maintain the valve structure in either a closed or open position, without maintaining continuous contact with the valve structure in order to maintain it in the preferred position.

Finally, another problem not satisfactorily addressed by known trocar assemblies is their general inability to allow a variety of predetermined medical instruments to pass through the interior of the trocar assembly, during the intended surgical procedure, without interfering with the structure and/or function of the flow regulating valve associated therewith.

Accordingly, there is a recognized need in the field of medical instrumentation for an improved trocar assembly incorporating a valve which may be selectively and easily positioned between a valve-open and a valve-closed position utilizing a single hand of the medical personnel operating trocar assembly. In addition, the design and structure of such an improved trocar assembly would enable the valve structure associated therewith to be maintained in either a valve-open or valve-closed position, without forcing the medical personnel to provide continuous contact therewith. Also such an improved trocar assembly should have sufficient structural versatility to allow a variety of different medical instruments to be used therewith in a manner which does not interfere with the structure of the valve assembly or its operation.

SUMMARY OF THE INVENTION

The present invention is directed to a trocar assembly which includes a valve assembly structured to be easily manipulated by a single hand of the physician, or other medical personnel operating the trocar assembly, such that the valve assembly can be efficiently oriented in either a valve-open or a valve-closed position.

More specifically, the trocar assembly of the present invention includes a housing having a substantially hollow interior and further including a somewhat conventional connector structure mountable thereon for interconnection with a source of pressurized fluid. The pressurized fluid may include, but is not limited to, carbon dioxide and is used to inflate internal body cavities of patients in order to facilitate the performance of laparoscopic, arthroscopic, endoscopic and like surgical procedures on a patient. The housing of the trocar assembly is connected at one end to an elongated open ended sleeve or cannula, which may serve as an access cannula disposable, through an incision, into communicating relation with the internal body cavity. The access cannula or sleeve is disposed and structured to allow passage there through of fluid so as to insufflate the internal body cavity and also to direct any one of a variety of different medical instruments to the surgical site.

An oppositely disposed end of the housing, relative to the cannula, is open and is structured to facilitate connection to a valve assembly. The valve assembly comprises a valve structure including a valve seat, integrally or otherwise fixedly secured to one another, so as to move as a single unit relative to the housing. The valve seat projects outwardly from one end of the valve structure and is disposed within the hollow interior of the housing. In addition, the aforementioned valve assembly also includes a valve member movably mounted within the hollow interior of the housing in cooperative relation to the valve seat. Accordingly, selective positioning of the valve seat relative to the valve member serves to define either a valve-open or a valve-closed position, dependent upon the orientation of the valve seat relative to the valve member.

The valve structure is rotatably connected to the housing in adjacent and substantially covering relation to the open end thereof. The fixed or integral connection between the valve seat and the valve structure causes the valve seat to rotate within the hollow interior of the housing when the valve structure is rotated. When so rotated, the valve seat may assume a variety of different orientations, at least one of which defines the aforementioned valve-closed position and at least one other of which defines the aforementioned valve-open position. The valve structure is at least partially mounted exteriorly of the hollow interior of the housing and is therefore readily accessible to the operator of the trocar assembly. In addition, at least one knob, flange, or like positioning member protrudes outwardly from the exterior of the valve structure to facilitate engagement by a thumb or other finger of the hand of the person holding and operating the trocar assembly. Accordingly manipulation of the valve structure to assume either the valve-open or valve-closed position may be accomplished by a single hand of the person holding and operating the trocar assembly.

In at least one embodiment of the present invention, the valve member and the valve seat are cooperatively disposed and structured to maintain substantially continuous engagement with one another, regardless or whether the valve seat and valve member are in the valve-closed or valve-open position. Therefore, a relatively small rotational displacement of the valve structure accomplishes disposition of the valve seat into fluid sealing engagement with the valve member to define the valve-closed position. Similarly the valve structure may be rotated only a minimal distance so as to displace the valve seat from the valve structure and dispose the valve assembly in at least a partially valve-open position. These relatively small rotational displacements of the valve structure and valve seat further facilitate a one handed manipulation of the valve assembly, while further facilitating holding and positioning the trocar assembly during the intended surgical procedure.

In addition, at least one embodiment of the present invention includes the provision of an adaptor structure which is connected to the valve structure exteriorly of the housing. The adaptor structure may be removably connected to the valve structure and replaced by one or more different types of adaptor structures for introduction of a variety of different instruments to the surgical procedure being performed. Regardless of the specific embodiment of the adaptor structure utilized, it is primarily designed to interconnect and/or "guide" predetermined medical instruments through a remainder of the trocar assembly. More specifically, one embodiment of the adaptor structure may be utilized to interconnect an obturator or penetrating needle to the trocar assembly. Similarly a biopsy needle may be interconnected to the trocar assembly in a similar manner. Either of the aforementioned medical instruments, as well as a variety of others, are attachable to one or more embodiments of the adaptor structure and extend through a central channel formed in the valve structure and extending through the valve seat. When such instrumentation is utilized, the valve member will be displaced from the valve seat if the valve seat and valve structure are in the valve-closed position. Alternatively, when the valve seat is disposed in an at least partially open position, the medical instrument may pass through the hollow interior of the housing and into and through the sleeve or access cannula connected to the housing.

When such medical instruments are utilized, appropriate gaskets or seals are associated with the adaptor structure to prevent inadvertent escape of the fluid introduced into the internal body cavity. Such a supplementary seal structure associated with the adaptor structure may be required, in that passage of a medical instrument through the valve assembly would necessitate either the valve assembly being selectively disposed in an open position or would force a displacement of the valve member out of sealing engagement with the valve seat.

Therefore, an improved trocar assembly of the present invention includes a valve assembly which is easily and efficiently manipulated by a single hand of medical personnel operating the trocar assembly. In addition, the valve assembly will automatically be maintained in either the valve-open or valve-closed position without maintaining contact with the valve structure or continuously applying force thereto.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 4 is a front perspective view shown in exploded form.

FIG. 5 is an end view taken along line 5—5 of FIG. 4.

Like reference numerals refer to like parts throughout the several views of the drawings.

DETAILED DESCRIPTION OF THE PREFERRED EMBODIMENT

Figure 1:
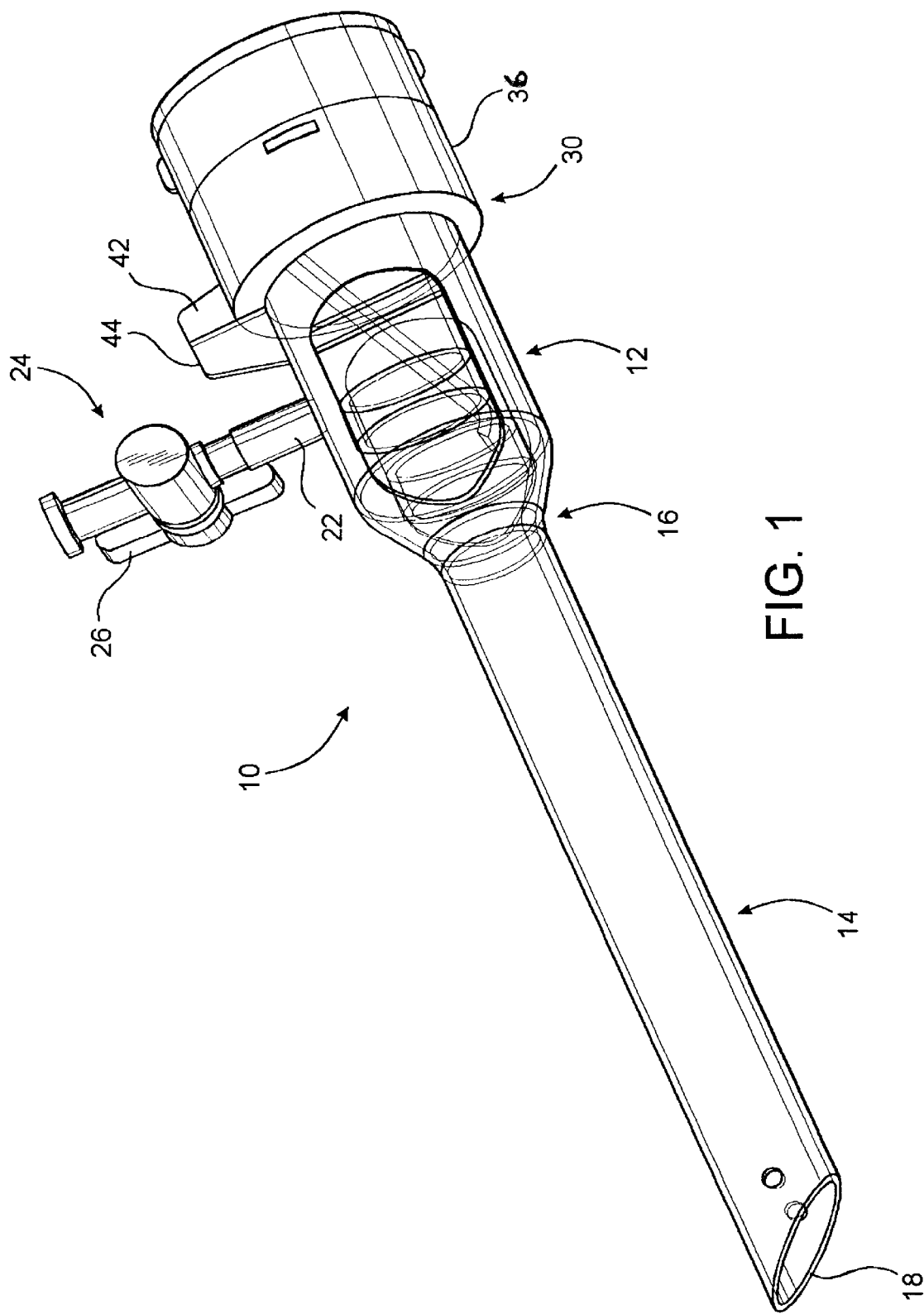
FIG. 1 is a perspective view of a trocar assembly of the present invention shown assembled and in a valve-closed position.

As demonstrated in the accompanying drawings, the present invention is directed to a trocar assembly generally indicated as 10 and including a housing generally indicated as 12 and an elongated hollow sleeve or cannula, generally indicated as 14 and attached to one end of the housing 12, as at 16. The opposite end 18 of the cannula 14 is open to allow the passage of medical instruments as well as fluid there through, as will be explained in greater detail hereinafter.

For purposes of clarity, the housing 12 is represented as being transparent. However, the material from which the housing, as well as the remaining trocar assembly 10, is formed may or may not be a transparent or translucent material. In any event, the housing 12 includes a substantially hollow interior having at least one open end 20 which is oppositely disposed to the cannula 14. The housing 12 may also include an access port or coupling 22 disposed and configured to receive a connector generally indicated as 24 for connection to a substantially conventional source of at least initially pressurized fluid. The fluid may be carbon dioxide or other commonly used gases, which are conventionally employed to inflate and expand the internal body cavity of a patient and thereby facilitate performance of the aforementioned of different types of surgical procedures by providing increased access to the body cavity. The connector 24 may include a control knob 26 which regulates fluid flow into the interior of the housing 12 through the connector 24 as is well known.

Figure 6:
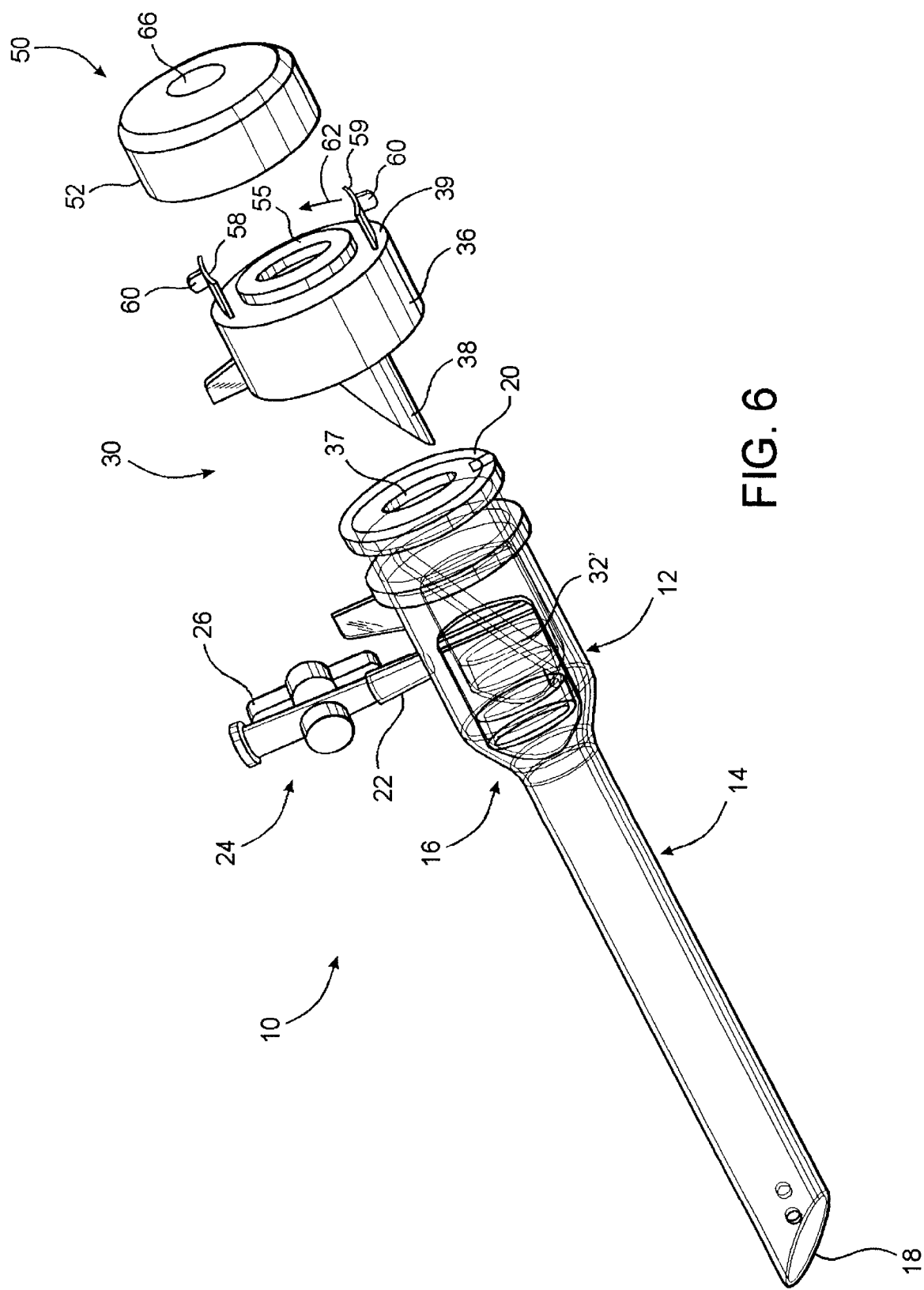
FIG. 6 is a rear perspective view shown in exploded form.

The present invention also includes a valve assembly generally indicated as 30. The valve assembly 30 comprises a valve member 32 secured to a mounting base 34 and a valve structure 36 having a valve seat 38 integrally or otherwise fixedly secured thereto. The valve member 32 is attached to the housing 12 independently of the valve structure 36 and valve seat 38. More specifically the mounting base 34 is disposed within the hollow interior of the housing 12 immediately adjacent to the open end 20, as best shown in FIG. 6. The valve member 32 is mounted within the hollow interior of the housing 12 and is dimensioned and configured to sealing engage the surrounding periphery 38' of the valve seat 38 to define the valve-closed position, as will be explained hereinafter.

The valve member 32 as well as the mounting base 34 may be integrally connected to one another and are formed of an elastomeric material preferably having an inherent bias. Further, the interconnection between the valve member 32 and the mounting base 34 forms an integral hinge as at 35 which serves to normally bias the valve member 32 in a inwardly oriented, substantially angled incline relative to an imaginary central longitudinal axis of the hollow interior of the housing 12. The elastomeric material from which the valve member 32 is formed allows it to be forced outwardly from its normally angled orientation, as shown in FIG. 2 and subsequently return to its normally "biased" position shown in FIG. 1, as will be explained in greater detail hereinafter.

It should be emphasized that while one embodiment of the present invention defines an integral connection between the valve member 32 and the mounting base 34, structural adaptations other than the integral hinge 35 are included within the intended spirit and scope of the present invention. For example, the valve member 32 may be connected by a variety of a different types of hinge structures (not shown for purposes of clarity) so as to facilitate the normal orientation of the valve member 32 in its angularly inclined position also disclosed FIGS. 4 and 6.

Figure 2:
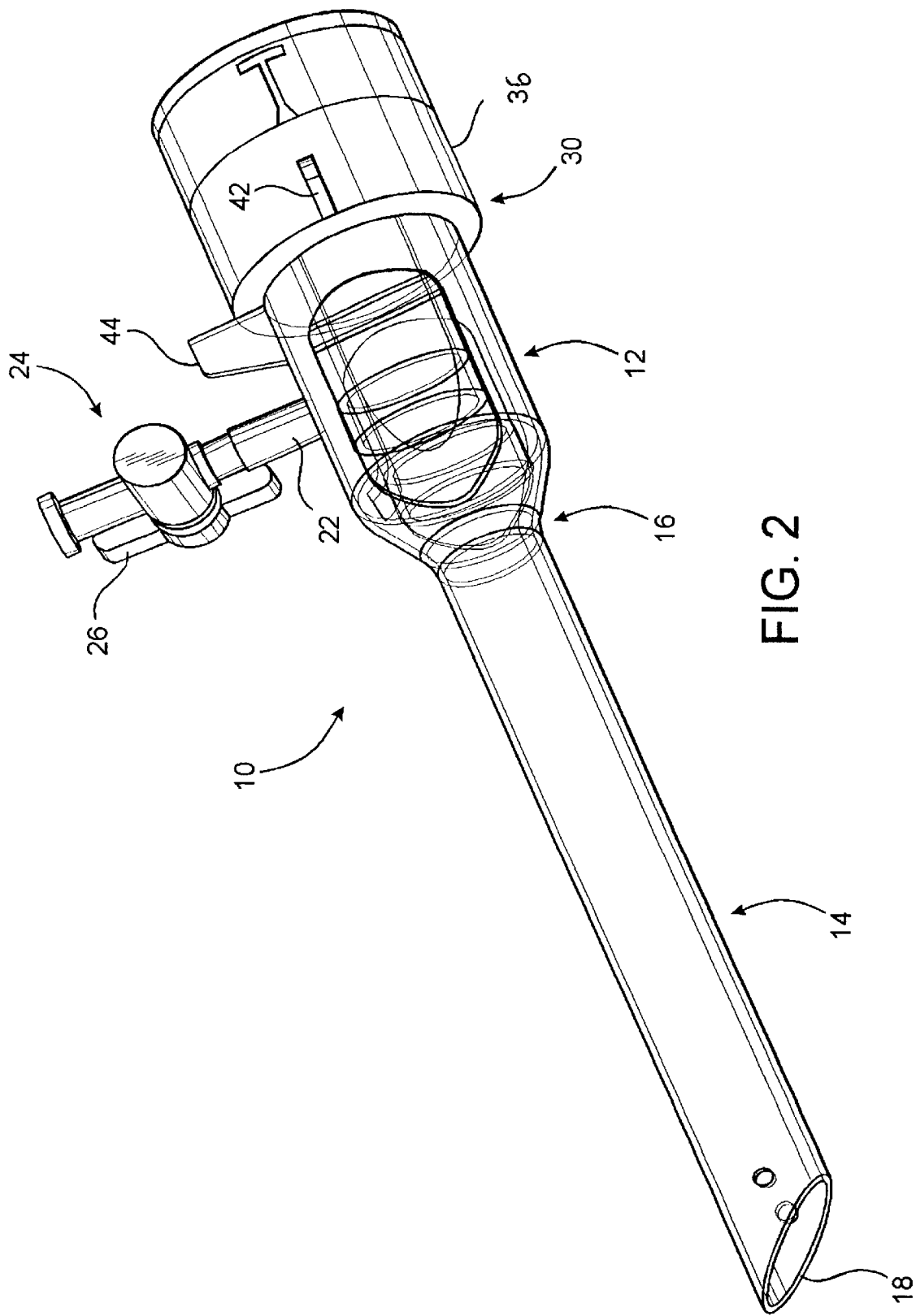
FIG. 2 is a perspective view of the trocar assembly of the present invention shown assembled and in a fully valve-open position.
Figure 3:
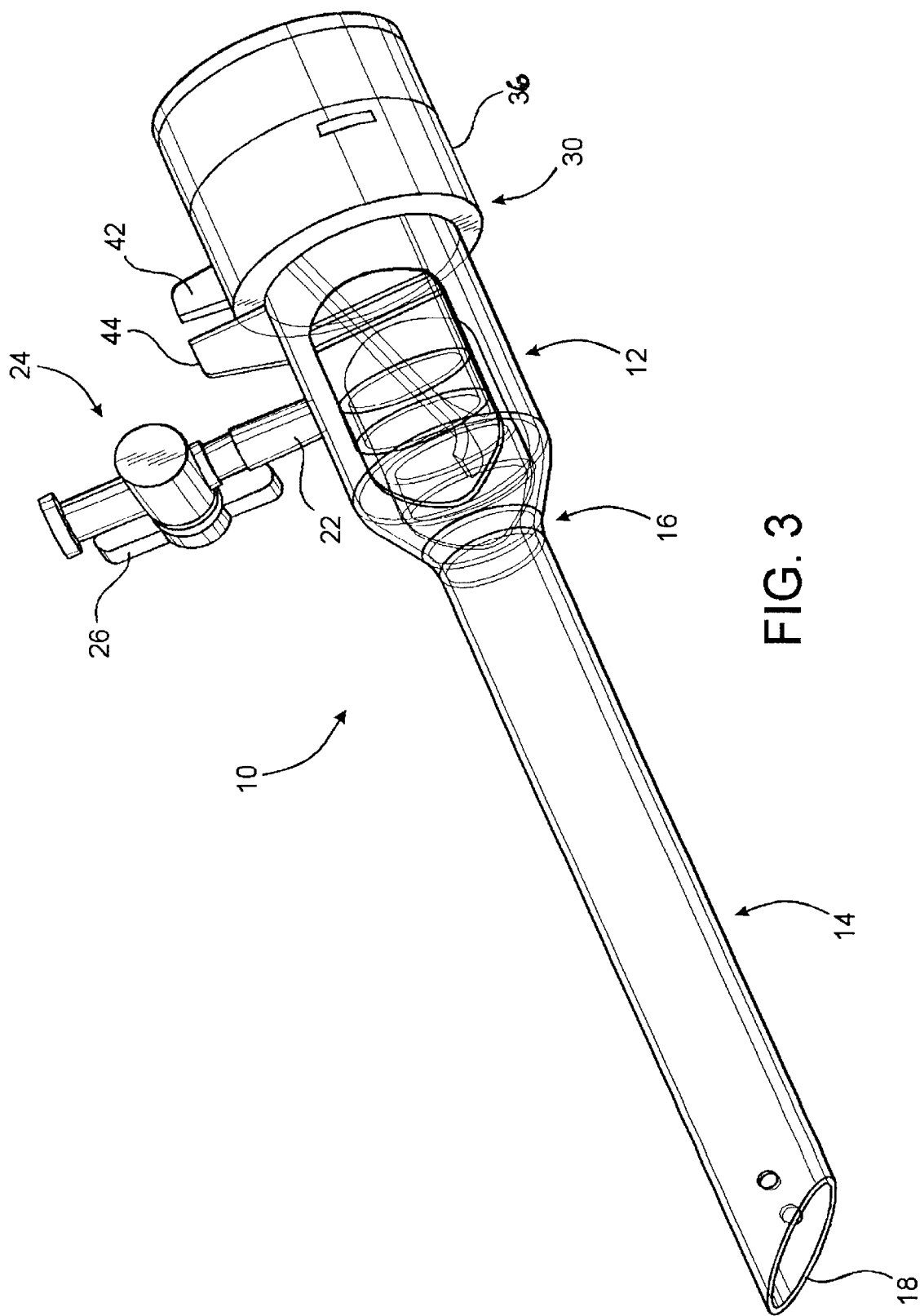
FIG. 3 is a perspective view of the trocar assembly of the present invention shown assembled and in a partially valve-open position.

Regardless of the specific movable interconnection between the valve member 32 and the mounting base 34, it is to be noted that the mounting base 34 includes an opening or aperture 37 of sufficient dimension to allow passage therethrough of the elongated valve seat 38, when in its assembled form as shown in FIGS. 1 through 3. Accordingly, upon connection of the mounting base 34 adjacent to the open end 20 of the hollow interior of the housing 12, the valve structure 36 and valve seat 38 are operatively assembled by passing the valve seat 38 into the hollow interior of the housing 12 and into cooperative relation to the valve member 32.

With reference to FIG. 4, the exterior periphery of the open end 20 includes thread like connector flanges 23, which allow at least a limited amount of rotation of the valve structure 36 relative to the housing 12 in each of two opposite directions as indicated by directional arrow 40. The connecting flanges 23 movably engage cooperatively formed structures (not shown for purposes of clarity) disposed on the interior of the valve structure 36, adjacent an access opening 36'. Therefore, it should be apparent that the valve structure 36, and the fixedly attached valve seat 38, are rotatable relative to the housing 12 in either of the two opposite directions, as indicated by directional arrow 40. Further, the relative disposition and configuration of the valve member 32 and the valve seat 38 serve to maintain these two elements in substantially continuous engagement with one another, as shown in FIGS. 1 through 3, regardless of whether the valve assembly 30 is selectively disposed in a valve-closed position as shown in FIG. 1 or a valve open-position as shown in FIG. 2. The versatility of the trocar assembly of the present invention is further emphasized by the ability of a user thereof to selectively dispose the valve assembly 30 in at least a partially open position, as shown in FIG. 3, rather than the closed position of FIG. 1 or the fully open position of FIG. 2.

Rotation of the valve structure 36 and valve seat 38 is facilitated by at least one outwardly projecting knob, flange, or like positioning member 42. The positioning member 42 extends outwardly from the exterior surface of the valve structure 36 and is disposed and dimensioned to be manipulated by the thumb or a single finger of a user's hand which serves to support and position the remainder of the trocar assembly 10. Also, a stop member 44 may be secured to the exterior surface of the housing 12 in interruptive engagement with the positioning member 42 so as to partially limit the rotation of the valve structure 36, as it is being selectively rotated relative to the housing 12 in order to open or close the valve assembly 30.

Additional structural features of the present invention include the mounting base 34 disposed in a seated or flush engagement with interior wall portions of the at least partially closed end 39 of the valve structure 36. However, while the valve structure 36 and valve seat 38 are selectively rotatable relative to the housing 12, the mounting base 34 and valve member 32 are not rotatable therewith. To the contrary, the mounting base 34 and attached valve member 32 are not rotatable relative to the housing 12 due to an interconnection between a key member 45 and a key slot 47. The key member 45 is integrally or otherwise fixedly secured to the housing 12 contiguous to the open end 20 and the key slot 47 is integrally formed about the outer periphery of the mounting base 34, as shown in FIGS. 4 and 5. It should be apparent therefore that is as the valve structure 36 and valve seat 38 rotate relative to the housing 12, the mounting base 34 and the valve member 32 are fixed in their indicated positions within the hollow interior of the housing 12, at least in terms of being non-rotatable relative to the housing 12.

As set forth above, the valve member 32 has a flexible, spring like hinge portion 35, which allows it to be moved into different angular orientations relative to an imaginary central longitudinal axis of the housing 12. Further, when the valve seat 38 is disposed in its operative, assembled position as shown in FIGS. 1 through 3, the valve member 32 and the valve seat 38 are disposed in substantially continuous engagement with one another. Moreover, rotation of the exteriorly disposed valve structure 38, such as by manipulation of the positioning member 42, will cause a sliding engagement between the exterior surface of the valve seat 38 and the under surface 32' of the valve member 32. The aforementioned valve-closed position of FIG. 1 is accomplished by the valve member 32 being disposed in a substantially fluid sealing engagement over the peripheral edge 38' of the valve seat 38, such that the entire periphery 38' is contacted by the undersurface 32' of the valve member 32 thereby preventing fluid flow to pass there between. To the contrary and with reference to FIGS. 2 and 3, rotation of the valve structure 38 causes a sliding engagement between either the exterior surface or surrounding periphery 38' of the valve seat 38 and the undersurface 32' of the valve member 32, which forces the valve member 32 outwardly from its normally biased, angularly oriented position of FIGS. 1 and 6. The maximum displacement of the valve member 32 is represented in the fully open position of FIG. 2 and a somewhat lesser displacement is represented by the partially valve-open position of FIG. 3.

Other structure included in at least one embodiment of the present invention comprises an adaptor member generally indicated as 50. The adaptor member 50 includes a cap member 52 removably or otherwise connected to the closed end 39 of the valve structure 36. A fluid seal is accomplished between the closed end 39 and the interior of the of the adaptor structure 50 by the provision of sealing gaskets 55 and 57, respectively formed on the exterior of the closed end 39 and the interior of the cap 52. Removable attachment between the cap 52 and the valve structure 36 is accomplished by outwardly extending, flexible fingers 58 and 59 having locking lugs 60 attached to the outer most ends thereof. The fingers 58 and 59 and their associated locking lugs 60 are formed of a flexible material and may be forced inwardly, in accordance with directional arrow 52. The fingers 58 and 59 are disposable to allow the locking lugs 60 to pass outwardly from the interior of the cap 52, through the receiving apertures 65. Manipulation of the fingers 58 and 59 and locking lugs 60 relative to the cap 52 facilitates removal of the cap 52 from the valve structure 36 so that it may be replaced by other adaptor members (not shown). The cap 52 of the adaptor member 50 includes a central passage 66 for the connection of a penetrating needle, biopsy needle, or other elongated medical instruments which successively passes through the cap 52, elongated channel formed on the interior of the valve structure 36, hollow interior of the housing 12 and along the length of the sleeve or cannula 14, so as to exit from the open end 18 thereof and participate, as intended, at the surgical site.

Additional structure associated with the trocar assembly 10 includes finger grips 70 secured to the exterior of the housing 30 and extending outwardly therefrom in substantially opposite directions. Finger grips 70 are used in conventional fashion to help secure the housing 12 as well as the cannula 14 in a proper position while manipulating a medical instrument, such as an obturator, as it penetrates into the exterior bodily tissue. Other medical instrumentation may also be similarly manipulated.

It should be apparent therefore that upon passage of the open end 18 of the cannula 14 into the interior of the internal body cavity, pressurized gas or fluid, such as carbon dioxide, is introduced therein causing an expansion thereof in order to provide better access thereto by the medical personnel. During such inflation and while the body cavity is maintained in its inflated state, the valve structure 36 of the valve assembly 30 is rotated so as to assume and maintain the valve-closed position, as shown in FIG. 1. While in the valve-closed position, a user of the trocar assembly 10 does not have to maintain any type continuous pressure on or contact with the positioning member 42 in order to maintain the valve-closed position. When it is intended to deflate the body cavity the positioning member 42 may be manipulated by the thumb or single finger of the hand holding the trocar assembly 10 and thereby rotate the valve structure 36 to assume the fully valve-open position of FIG. 2 or the partially valve-open position of FIG. 3.

When it is required to insert a medical instrument through the adaptor member 50 and beyond the valve assembly 30, the valve member 32 may be automatically forced away from its sealing orientation relative to the periphery 38' of the valve seat 38 by the leading end of the instrument passing through the valve seat 38. Alternatively, the valve structure 36 may be rotated to the fully or partially valve-open position shown in FIGS. 2 and 3 respectively in order to facilitate passage of any medical instrument through and beyond the valve assembly 30 and into the cannula 14 so that it can reach the surgical site.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A trocar assembly structured to facilitate fluid flow and disposition of medical instrumentation into and out of a body cavity of a patient, said trocar assembly comprising:
    a) a housing including a hollow interior and a first open end,
    b) a valve member movably mounted within said hollow interior,
    c) a valve structure rotatably connected to said housing adjacent to said open end and including a valve seat,
    d) said valve seat connected to said valve structure and rotatable therewith within said hollow interior relative to said valve member,
    e) said valve member disposed in substantially continuous engagement with said valve seat and into and out of fluid sealing engagement with said valve seat dependent on an orientation of said valve seat relative to said valve member, and
    f) said valve member and said valve seat disposable between a valve-open position and a valve-closed position upon selective rotation of said valve structure relative to said housing.

2. A trocar assembly as recited in claim 1 wherein said valve structure is at least partially disposed exteriorly of said housing in accessible relation to a user thereof.

3. A trocar assembly as recited in claim 2 comprising an adaptor member removably attached to said valve structure and secured thereto so as to rotate therewith relative to said housing, said adaptor member structured to facilitate interconnection of the medical instrumentation to said housing.

4. A trocar assembly as recited in claim 1 wherein said valve member includes a mounting base connected thereto, said valve member movable relative to said mounting base and said valve seat between said valve open and said valve closed positions.

5. A trocar assembly as recited in claim 4 further comprising a hinge movably interconnecting said valve member and said mounting base and cooperatively structured therewith to normally bias said valve member towards said valve closed position.

6. A trocar assembly as recited in claim 5 wherein said valve member, said mounting base and said hinge collectively comprise an integral, one piece construction.

7. A trocar assembly as recited in claim 6 wherein at least said hinge is formed of an elastomeric material.

8. A trocar assembly as recited in claim 5 wherein said valve member, said mounting base and said hinge collectively comprise an integral, one-piece construction formed of an elastomeric material.

9. A trocar assembly as recited in claim 5 wherein said mounting base is connected to said housing and disposed in at least partially surrounding relation to said valve seat.

10. A trocar assembly comprising:
   a) a housing having a hollow interior and including at least one open end, an elongated sleeve secured to said housing substantially opposite to said open end,
   b) a valve member connected to said housing and disposed within said hollow interior,
   c) a valve structure movably connected to said housing and a valve seat connected to said valve structure and movable therewith, and
   d) said valve seat disposed in continuous engagement with said valve member and movable relative to said valve member into either a valve open position or a valve closed position.

11. A trocar assembly as recited in claim 10 wherein said valve seat is selectively rotatable within said hollow interior and into substantially sealing engagement with said valve member to define said valve-closed position.

12. A trocar assembly as recited in claim 10 wherein said valve seat is selectively rotatable within said hollow interior and out of sealing engagement with said valve member to define said valve open position.

13. A trocar assembly as recited in claim 12, wherein said valve seat is selectively rotatable within said hollow interior and into substantially sealing engagement with said valve member to define said valve-closed position.

14. A trocar assembly as recited in claim 10, further comprising an adaptor member structured to secure a predetermined instrument to said housing and direct said predetermined instrument through said hollow interior and into and along the length of said sleeve.

15. A trocar assembly as recited in claim 10 wherein said open end is disposed and dimensioned to receive passage of said valve seat there through and attachment of said valve structure in substantially covering relation to said open end.

16. A trocar assembly as recited in claim 15 wherein said valve structure is at least partially disposed exteriorly of said housing in accessible relation to a user thereof.

17. A trocar assembly as recited in claim 16 wherein said valve structure is rotatably connected to said housing adjacent said open end, said valve seat with said valve structure within said housing and relative to said valve member.

18. A trocar assembly as recited in claim 17 wherein said valve member is disposable between said valve-open position and said valve-closed position upon selective rotation of said valve structure relative to said housing.

19. A trocar assembly as recited in claim 10 further comprising an adaptor member connected to said valve structure and structured to facilitate interconnection of a predetermined instrument to said housing.

20. A trocar assembly as recited in claim 19 wherein said adaptor member is removably attached to said valve structure and secured thereto so as to rotate therewith relative to said housing.

21. A trocar assembly as recited in claim 20 wherein said valve structure includes a channel formed on an interior thereof, said channel surrounded by said valve seat and disposed in aligned, communicating relation with said hollow interior of said housing and an interior of said sleeve along a length thereof.

22. A trocar assembly as recited in claim 21 wherein said adaptor member is disposed and structured to direct said predetermined instrument successively through said channel of said valve structure, said valve seat, said hollow interior of said housing and along substantially the entire length of said sleeve, when said valve member is in said valve-open position.

23. A trocar assembly as recited in claim 10 further comprising a mounting base and a hinge movably interconnecting said valve member to said mounting base, said hinge structured to normally bias said valve member into said continuous engagement with said valve seat.

24. A trocar assembly as recited in claim 23 wherein at least said hinge is formed of an elastomeric material.

25. A trocar assembly as recited in claim 23 wherein said valve member, said mounting base and said hinge collectively comprise an integral, one-piece construction formed at least in part from an elastomeric material.

26. A trocar assembly as recited in claim 23 wherein said mounting base is connected to said housing and disposed in at least partially surrounding relation to said valve seat; said valve seat rotatable relative to said mounting base.

27. A trocar assembly comprising:
   a) a housing having a hollow interior and including at least one open end, an elongated sleeve secured to said housing in communicating relation with said hollow interior,
   b) a valve member disposed within said housing,
   c) a valve seat disposed within said housing and rotatable relative to said valve member, and
   d) said valve seat selectively positionable relative to said valve member between a valve closed position and a valve open position.

28. A trocar assembly as recited in claim 27 further comprising a valve structure connected to said valve seat and movable therewith, said valve structure at least partially disposed on an exterior of said housing in an accessible location.

29. A trocar assembly as recited in claim 27 wherein said valve member includes a mounting base connected thereto, said valve member movable relative to said mounting base and said valve seat between said valve open and valve closed positions.

30. A trocar assembly as recited in claim 29 further comprising a hinge movably interconnecting said valve member and said mounting base and cooperatively structured therewith to normally bias said valve member towards said valve closed position.

31. A trocar assembly as recited in claim 30 wherein at least said hinge is formed of an elastomeric material.

32. A trocar assembly as recited in claim 30 wherein said valve member, said mounting base and said hinge collectively comprise an integral, one-piece construction at least partially formed of an elastomeric material.

33. A trocar assembly as recited in claim 29 wherein said mounting base is connected to said housing and disposed in at least partially surrounding relation to said valve seat, said valve seat rotatable relative to said mounting base into and out of fluid sealing engagement with said valve member.

34. A trocar assembly as recited in claim 27 wherein said valve seat and said valve member are maintained in continuous engagement with one another concurrent to positioning said valve seat into and between said valve closed and valve open positions.

35. A trocar assembly as recited in claim 34 wherein said continuous engagement is at least partially defined by an exterior surface of said valve seat being disposed in sliding engagement with said valve member as said valve seat is disposed between said valve closed and valve open positions.

* * * * *